(12) United States Patent
Lau

(10) Patent No.: US 12,408,941 B2
(45) Date of Patent: Sep. 9, 2025

(54) VESSEL HARVESTING APPARATUS AND METHOD

(71) Applicant: Maquet Cardiovascular LLC, Wayne, NJ (US)

(72) Inventor: Liming Lau, Mountain View, CA (US)

(73) Assignee: MAQUET CARDIOVASCULAR LLC, Wayne, NJ (US)

( * ) Notice: Subject to any disclaimer, the term of this patent is extended or adjusted under 35 U.S.C. 154(b) by 273 days.

(21) Appl. No.: 17/899,568

(22) Filed: Aug. 30, 2022

(65) Prior Publication Data

US 2023/0134921 A1 May 4, 2023

Related U.S. Application Data

(63) Continuation of application No. 15/870,823, filed on Jan. 12, 2018, now Pat. No. 11,432,839.

(51) Int. Cl.
*A61B 18/14* (2006.01)
*A61B 17/00* (2006.01)
(Continued)

(52) U.S. Cl.
CPC .. *A61B 17/32053* (2013.01); *A61B 17/00008* (2013.01); *A61B 17/0218* (2013.01); *A61B 17/320016* (2013.01); *A61B 17/320092* (2013.01); *A61B 18/082* (2013.01); *A61B 18/1445* (2013.01); *A61B 18/1477* (2013.01); *A61B 90/361* (2016.02); *A61B 2017/00296* (2013.01); *A61B 2017/00778* (2013.01); *A61B 2017/00907* (2013.01); *A61B 2017/320056* (2013.01); *A61B 2017/320078* (2017.08);
(Continued)

(58) Field of Classification Search
CPC .......... A61B 17/32053; A61B 17/0218; A61B 17/320016; A61B 17/320092; A61B 18/082; A61B 18/1445; A61B 2018/00589; A61B 17/00008; A61B 18/1477; A61B 2018/00196; A61B 2018/00577; A61B 2018/00601; A61B 2018/0063; A61B 2018/00982; A61B 2018/1475; A61B 90/361; A61B 2017/00296; A61B 2017/00778; A61B 2017/00907; A61B 2017/320056; A61B 2017/320078; A61B 2017/320095
See application file for complete search history.

(56) References Cited

U.S. PATENT DOCUMENTS 4,793,346 A * 12/1988 Mindich .......... A61B 17/00008
606/180
5,053,041 A * 10/1991 Ansari .................. A61B 17/29
606/1
(Continued)

*Primary Examiner* — Tan-Uyen T Ho
*Assistant Examiner* — Osama Nemer
(74) *Attorney, Agent, or Firm* — Fay Kaplun & Marcin, LLP

(57) ABSTRACT

An apparatus for harvesting a vessel from a body, includes: a cannula having a dissector for advancing along the vessel to create a tunnel, the dissector having a transparent portion; and an energy tool moveably coupled to the cannula, wherein the energy tool is configured to separate a pediculated vessel having at least a segment of the vessel and a pedicle around the segment of the vessel from surrounding tissue, and wherein at least a part of the energy tool is visible through the transparent portion of the dissector during use of the energy tool.

13 Claims, 11 Drawing Sheets

(51) Int. Cl.
  *A61B 17/02* (2006.01)
  *A61B 17/32* (2006.01)
  *A61B 17/3205* (2006.01)
  *A61B 18/00* (2006.01)
  *A61B 18/08* (2006.01)
  *A61B 90/00* (2016.01)

(52) U.S. Cl.
  CPC ............ *A61B 2017/320095* (2017.08); *A61B 2018/00196* (2013.01); *A61B 2018/00577* (2013.01); *A61B 2018/00589* (2013.01); *A61B 2018/00601* (2013.01); *A61B 2018/0063* (2013.01); *A61B 2018/00982* (2013.01); *A61B 2018/1475* (2013.01)

(56) References Cited

U.S. PATENT DOCUMENTS

| | | | | |
|---|---|---|---|---|
| 5,549,623 A * | | 8/1996 | Sharpe | A61B 17/3201 606/174 |
| 5,569,291 A * | | 10/1996 | Privitera | A61B 17/3417 606/185 |
| 5,667,480 A * | | 9/1997 | Knight | A61B 17/00234 606/190 |
| 5,810,806 A * | | 9/1998 | Ritchart | A61B 10/0266 606/41 |
| 5,830,222 A * | | 11/1998 | Makower | A61B 17/1219 623/1.11 |
| RE36,043 E * | | 1/1999 | Knighton | A61B 1/018 600/101 |
| 5,873,889 A * | | 2/1999 | Chin | A61B 17/00008 606/190 |
| 5,916,233 A * | | 6/1999 | Chin | A61B 17/00008 606/190 |
| 5,976,168 A * | | 11/1999 | Chin | A61B 17/320016 606/190 |
| 6,951,568 B1 * | | 10/2005 | Chin | A61B 1/00089 606/190 |
| 7,485,092 B1 * | | 2/2009 | Stewart | A61B 17/0218 600/176 |
| 7,601,125 B1 * | | 10/2009 | Kai | A61B 10/0266 600/564 |
| 7,699,861 B2 * | | 4/2010 | Bayer | A61B 17/00008 606/159 |
| 7,981,127 B2 * | | 7/2011 | Kasahara | A61B 17/0218 606/190 |
| 7,981,133 B2 * | | 7/2011 | Chin | A61B 17/00008 606/190 |
| 9,700,398 B2 * | | 7/2017 | Stewart | A61B 18/1445 |
| 9,730,782 B2 * | | 8/2017 | Stewart | A61B 17/3201 |
| 9,833,308 B2 * | | 12/2017 | Dye | A61B 17/00234 |
| 10,299,770 B2 * | | 5/2019 | Willis | A61B 1/3137 |
| 11,432,839 B2 * | | 9/2022 | Lau | A61B 17/320092 |
| 2003/0065351 A1 * | | 4/2003 | Hess | A61B 17/00008 606/190 |
| 2006/0217706 A1 * | | 9/2006 | Lau | A61B 18/085 606/45 |
| 2007/0276418 A1 * | | 11/2007 | Kadykowski | A61B 17/00008 606/159 |
| 2008/0306335 A1 * | | 12/2008 | Lau | A61B 1/00135 600/106 |
| 2009/0023986 A1 * | | 1/2009 | Stewart | A61B 18/148 606/190 |
| 2010/0191043 A1 * | | 7/2010 | Chin | A61B 17/00008 600/36 |
| 2011/0046624 A1 * | | 2/2011 | Lin | A61B 18/1442 606/51 |
| 2012/0078037 A1 * | | 3/2012 | Stewart | A61B 17/3201 600/36 |
| 2013/0102843 A1 * | | 4/2013 | Feuer | A61B 1/00087 600/114 |
| 2013/0274548 A1 * | | 10/2013 | Fels | A61B 1/0684 600/104 |
| 2015/0164488 A1 * | | 6/2015 | Stewart | A61B 17/320016 600/36 |
| 2015/0164632 A1 * | | 6/2015 | Stewart | A61B 17/00008 600/36 |
| 2016/0045216 A1 * | | 2/2016 | Langford | A61B 17/00008 606/29 |
| 2016/0199090 A1 * | | 7/2016 | Stewart | A61B 18/1482 606/46 |
| 2017/0020546 A1 * | | 1/2017 | Chin | A61B 17/3417 |
| 2017/0035487 A1 * | | 2/2017 | Kadykowski | A61B 18/04 |
| 2017/0100107 A1 * | | 4/2017 | Takashi | A61B 1/00195 |
| 2019/0216489 A1 * | | 7/2019 | Lau | A61B 18/082 |
| 2020/0345408 A1 * | | 11/2020 | Orphanos | A61B 18/14 |

* cited by examiner

1300

Item 1304

Creating an endoscopic space adjacent to a vessel to be harvested by a dissector, the dissector having a transparent portion Item 1306

Separating a pediculated vessel having at least a segment of the vessel and a pedicle around the segment of the vessel by an energy tool, wherein at least a part of the energy tool is visible through the transparent portion of the dissector while the energy tool is being used

FIG. 13

VESSEL HARVESTING APPARATUS AND METHOD

RELATED APPLICATIONS

This application is a continuation of U.S. patent application Ser. No. 15/870,823, filed Jan. 12, 2018, now U.S. Pat. No. 11,432,839.

FIELD

An embodiment described herein relates to a surgical instrument and its use, and more particularly, to a surgical instrument for use in a vessel harvesting procedure.

BACKGROUND

Coronary artery bypass grafting (CABG) is a well-established surgical procedure in which arterial blockages of the heart are bypassed using autologous blood vessels (hereafter referred to as bypass conduits). Commonly-used autologous blood vessels for bypass include the internal thoracic artery, the radial artery, and the greater saphenous vein. Patency of the graft is greatly influenced by bypass conduit selection, surgical strategies and anastomotic techniques, patient characteristics such as disease state and comorbidities, in addition to numerous other factors.

Efforts to improve the patency of bypass conduits have focused on aspects such as the type of blood vessel used (arterial or venous) and method of harvest (open or endoscopic). Although attached internal thoracic artery grafts remain the gold standard with respect to long-term patency, they are limited in length, and thus in the number of bypasses that can be completed with each internal thoracic artery. For patients undergoing multiple bypasses in one operation, or repeat bypass surgery, radial artery and/or greater saphenous vein free grafts often are needed. These blood vessels are harvested either via open surgical access by making an incision through the skin over the entire length of vessel to be harvested, or less-invasively through the use of endoscopic devices.

Endoscopic vessel harvest (EVH) has been adopted as the standard of care in many parts of the world due to a substantial reduction in morbidity at the vessel harvest site and corresponding economic benefit, as well as other advantages such as improved cosmetics. However, concerns remain amongst some clinicians about the impact of EVH on conduit quality and about the use of venous conduits on long-term CABG patency. The quality of endoscopically-harvested bypass conduits may be affected by EVH device selection, endoscopic harvesting techniques, and post-harvest conduit handling. Consequently, advanced devices, refined techniques, and improved user training programs have been developed to address the weaknesses of the early EVH experience. Meanwhile, clinical evidence has also emerged suggesting that venous conduits harvested with their surrounding perivascular tissue (hereafter referred to as the tissue pedicle) rather than as skeletonized vessels per current practices can lead to improved long-term bypass graft patency. These pediculated or "no-touch" harvesting techniques, which are already employed for internal thoracic artery harvests, are believed to improve long-term performance of venous conduits by protecting the vessel from mechanical trauma during harvest, providing structural support to the conduit and allowing perfusion of the conduit wall upon arterialization, and facilitating beneficial biochemical processes such as nitric oxide release.

Although pediculated vessel harvest can be performed using commercially-marketed devices for EVH such as VASOVIEW HEMOPRO (Getinge Aft Sweden), existing device designs and published instructions for use have not been specifically optimized to accomplish removal of the tissue pedicle, and published clinical data for pediculated venous bypass conduits have employed conduits harvested via open surgical access. New apparatus and method for vessel harvesting that addresses the weaknesses of early or current EVH techniques are described herein.

SUMMARY

An apparatus for harvesting a vessel from a body, includes: a cannula having a dissector for advancing along the vessel to create a tunnel, the dissector having a transparent portion; and an energy tool moveably coupled to the cannula, wherein the energy tool is configured to separate a pediculated vessel having at least a segment of the vessel and a pedicle around the segment of the vessel from surrounding tissue, and wherein at least a part of the energy tool is visible through the transparent portion of the dissector during use of the energy tool.

Optionally, the energy tool has a retracted position and an extended position.

Optionally, the energy tool is configured to deflect towards a longitudinal axis of the apparatus as the energy tool moves from the retracted position to the extended position.

Optionally, the energy tool is slidably coupled to the cannula so that the energy tool is slidable along a direction that is parallel to a longitudinal axis of the cannula.

Optionally, the energy tool is steerable.

Optionally, the energy tool has an arcuate tip, a blunt tip, or a spatulate tip.

Optionally, the energy tool has forceps-type jaws.

Optionally, the energy tool is moveable along a curvilinear path circumferentially around a longitudinal axis of the cannula.

Optionally, the energy tool is rotatable to modify its orientation with respect to a longitudinal axis of the cannula.

Optionally, the apparatus further includes an imaging device, wherein the energy tool is moveable to a position distal to a distal end of the imaging device.

Optionally, the apparatus further includes a retractor moveably coupled to the cannula, wherein the retractor is configured to engage with the pediculated vessel.

Optionally, the apparatus further includes an imaging device, wherein the retractor is moveable to a position distal to a distal end of the imaging device.

Optionally, the cannula has a first side and a second side opposite from the first side, and wherein retractor is located closer to the first side of the cannula than to the second side of the cannula, and the energy tool is located closer to the second side of the cannula than to the first side of the cannula.

Optionally, the retractor is configured to deflect away from a longitudinal axis of the apparatus as the retractor moves from a retracted position to an extended position.

Optionally, the retractor is configured to change from a lower-profile when in a retracted position, to a larger-profile when in an extended position.

Optionally, the energy tool comprises an edge configured to cut tissue.

Optionally, the energy tool comprises a ring-shape structure.

Optionally, the ring-shape structure is mounted to a rod.

Optionally, the energy tool comprises a first heating element at a leading end of the ring-shape structure, and a second heating element at a circumferential exterior surface of the ring-shape structure for providing energy to control bleeding.

Optionally, the energy tool is configured to provide ultrasonic energy for tissue separation and/or sealing.

Optionally, the energy tool is configured to provide heat for tissue separation and/or sealing.

Optionally, the energy tool is configured to provide radiofrequency energy for tissue separation and/or sealing.

Optionally, the energy tool comprises a commercially available energy instrument that is detachably coupled to the cannula.

Optionally, the cannula comprises a lumen configured to house a first imaging device.

Optionally, the energy tool is located distal to a distal end of the lumen.

Optionally, the apparatus further includes the first imaging device.

Optionally, the first imaging device comprises an endoscope.

Optionally, the first imaging device comprises an electronic image sensor.

Optionally, the first imaging device comprises a distal end, and wherein an axis extending from the distal end of the imaging device to the energy tool traverses the transparent portion of the dissector.

Optionally, the apparatus further includes a second imaging device, wherein the first imaging device is configured for visualization of tissue dissection by the dissector, and the second imaging device is configured for visualization of an operation being performed by the energy tool.

Optionally, the apparatus has a central axis extending along a longitudinal length of the apparatus, the dissector is located at a first longitudinal axis offset from the central axis, and the energy tool is located at a second longitudinal axis offset from the central axis, the second longitudinal axis being different from the first longitudinal axis.

A method for harvesting a vessel from a body, includes: creating, by an apparatus, a tunnel from a skin incision for harvesting a vessel; and separating, by an energy tool, a pediculated vessel having at least a segment of the vessel and a pedicle around the segment of the vessel, wherein at least a part of the energy tool is visible through a transparent portion of the apparatus while the energy tool is being used.

Other and further aspects and features will be evident from reading the following detailed description of the embodiments, including the appended drawings.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict exemplary embodiments and are not therefore to be considered limiting in the scope of the claims.

FIGS. 10C-12 illustrate additional images from an imaging device viewing through the dissector of the apparatus of FIG. 2 during the vessel harvesting procedure.

FIG. 13 illustrates a method of vessel harvesting.

DETAILED DESCRIPTION

Figure 1:
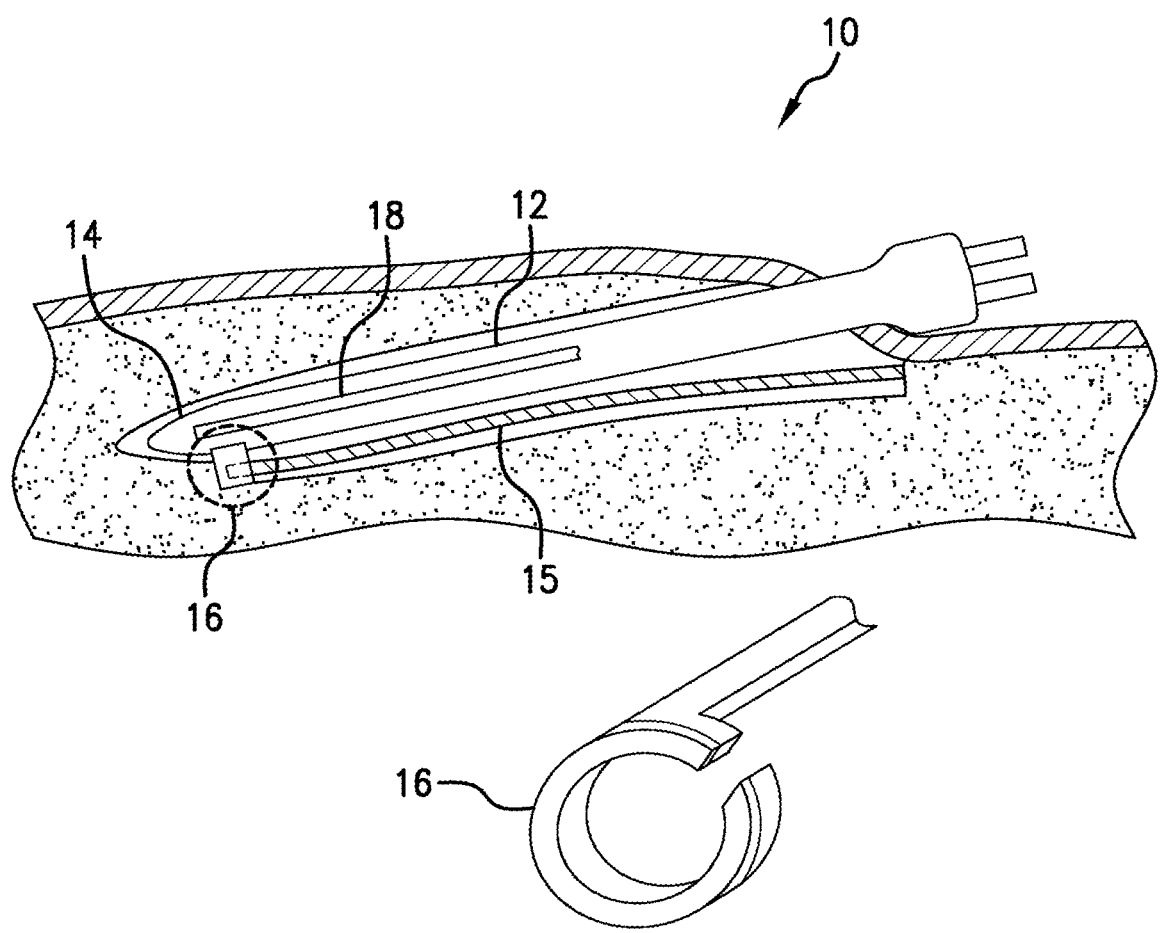
FIG. 1 illustrates an apparatus for harvesting a vessel.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the embodiments of the disclosure or as a limitation on the scope of the inventions disclosed herein. In addition, an illustrated embodiment does not need to have all the aspects or advantages shown. An aspect or an advantage described in conjunction with a particular embodiment is not necessarily limited to that embodiment and can be practiced in any other embodiments even if not so illustrated or explicitly described.

FIG. 1 illustrates an apparatus 10 for harvesting a vessel. The apparatus 10 has a sheath 12, and a dissector tip 14 at one end of the sheath 12. The dissector tip 14 is configured to be inserted into a patient through a skin incision, and be advanced along a target vessel 15. The apparatus 10 also has a cutting element 16 with a ring shape. The ring-shape cutting element 16 is configured for placement circumferentially around the target vessel 15, and to separate the tissue circumscribed by the cutting element 16 from its surrounding tissue, as the sheath 12 is advanced in a forward (or distal) direction along the target vessel 15. The apparatus 10 also has an endoscope 18 housed in the sheath 12. The endoscope 18 has a forward view through a transparent portion of the tip 14. The apparatus 10 has several drawbacks with respect to its clinical safety and effectiveness.

First, in the apparatus 10, because the distal end of the endoscope 18 is located distal to the cutting element 16, the cutting element 16 is entirely out of the field of view of the endoscope 18. Accordingly, while the cutting element 16 is being used to separate tissue, the user of the apparatus 10 cannot see the tissue that is being cut, nor can the user see the cutting element 16. Thus, the apparatus 10 poses substantial risks in terms of clinical safety and effectiveness. In particular, because the user cannot see the tissue being operated on, there are substantial risks of unintended mechanical or thermal damage to the target vessel and surrounding tissues, including inadvertent severing of the target vessel.

In addition, the ring shape cutting element 16 in the apparatus 10 is configured to always hold the target vessel between the field of view of the endoscope 18 and a portion of the cutting element 16. Accordingly, even if the apparatus 10 is modified to move the endoscope 18 proximally, so that the lens of the endoscope 18 is proximal to the cutting element 16, the above visualization problem still exists. In particular, due to the geometry of the cutting element 16, and the way that it is configured to separate tissue, the endoscope 18 cannot see the underside of the target vessel, nor can it see the bottom half of the cutting element 16 (because the target vessel will block the view of the endoscope 18).

Also, when using the apparatus 10, the energy at the cutting element 16 is always activated during dissection. If the cutting element 16 were not activated during dissection, the tissue would be bluntly dissected solely by the pressure applied by the cutting element, and all blood vessels encountered within would be avulsed, resulting in bleeding. Accordingly, use of the apparatus 10 will require simultaneously cutting and sealing of vessel branches extending from the target vessel as the dissector tip 14 advances. In addition, because the cutting element 16 is always activated, to reduce the risk of thermal injury to target vessel, use of the apparatus 10 will require a single-pass maneuver, in which the cutting element 16 is always moved continuously distally. However, in an EVH procedure, even to achieve exposure of the upper/anterior surface of the vessel, the dissection process may involve repeated, small-scale, back-and-forth movements in a localized area. The user may also perform frequent pauses to identify tissues and to ascertain correct direction for device advancement. Thus, an EVH procedure using the continuously-activated heating element 16 of the apparatus 10 is likely to result in increased thermal exposure (due to a continuously activated cutting element 16 that is moved back-and-forth, or that is paused, next to target vessel), and consequently increasing the risk of inadvertent thermal damage to the target vessel.

Also, because the tissue being separated by the cutting element 16 is not visible to the user of the apparatus 10, the user will not have sufficient information to make any adjustment in the speed of the movement of the cutting element 16 and/or any adjustment in the energy parameters for the cutting element 16. For example, if there is a large vessel branch that is below the target vessel, the user will not be able to see the large branch because it is obscured from view by the target vessel. The user also will not be able to see the cutting element 16 treating the large branch because the contact point between the cutting element 16 and the large branch under the target vessel is likewise obscured from the view of the endoscope 18. Accordingly, the user will not be able to make an adjustment by reducing the forward rate of advancement of the cutting element 16 to allow for slower coagulation (sealing) of the large vessel branch. This may result in uncontrolled bleeding at the target site.

Furthermore, the ring geometry of the cutting element 16 in the apparatus 10 poses another problem. In some cases, during the procedure, the user may encounter a large vessel branch. In such cases, the user may reduce speed of movement of the cutting element 16 accordingly to attempt to create a seal for the large branch. However, because all of the tissue to be cut is contacted by the energized ring-shape region of the cutting element 16, all of the tissue surrounded by the cutting element 16 including the target vessel would be subjected to increased thermal exposure (due to the slower movement of the cutting element 16). This will create unintended thermal injury to the harvested vessel. The above assumes that the user of the apparatus 10 can see the large vessel branch. If the vessel branch is out of the view of the endoscope, the user cannot even see the vessel branch in time to make any adjustment in the energy delivery parameter. This can lead to an inadequate sealing of the vessel branch, and may even lead to conversion of the endoscopic procedure into open surgery due to loss of visibility from excessive blood in the endoscopic field from the inadequate sealing of the vessel branch.

Lastly, the ring geometry of the cutting element 16 has a fixed cross sectional opening that limits the tissue to be dissected to have a fixed pre-determined cross sectional dimension. Individual anatomical variations may present, such as parallel vein segments, which cannot be accommodated by the apparatus 10 without significant risk of unintended tissue injury or surgical error.

Figure 2A:
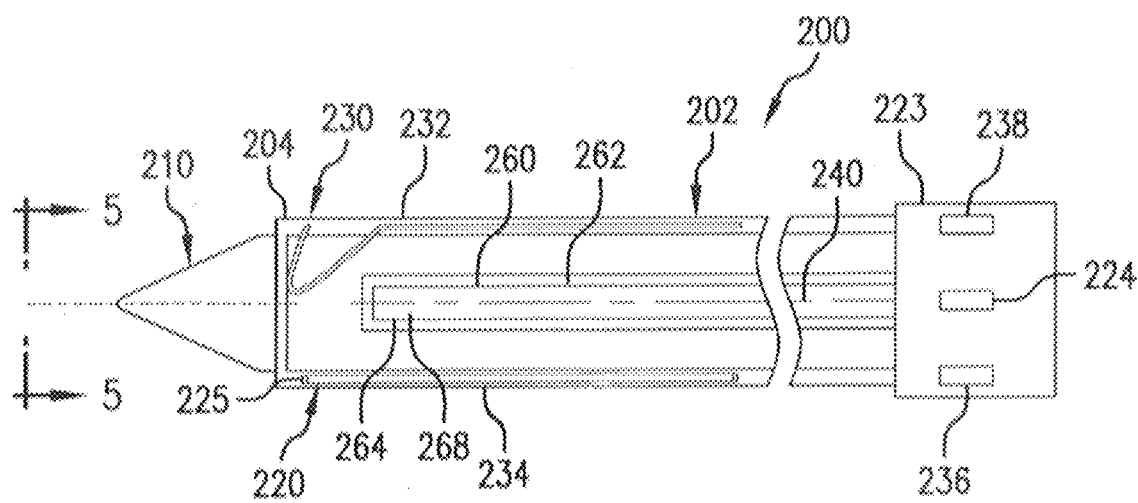
FIG. 2A illustrates another apparatus for harvesting a vessel, particularly showing the apparatus having a retractor and an energy tool in retracted configurations.
Figure 2B:
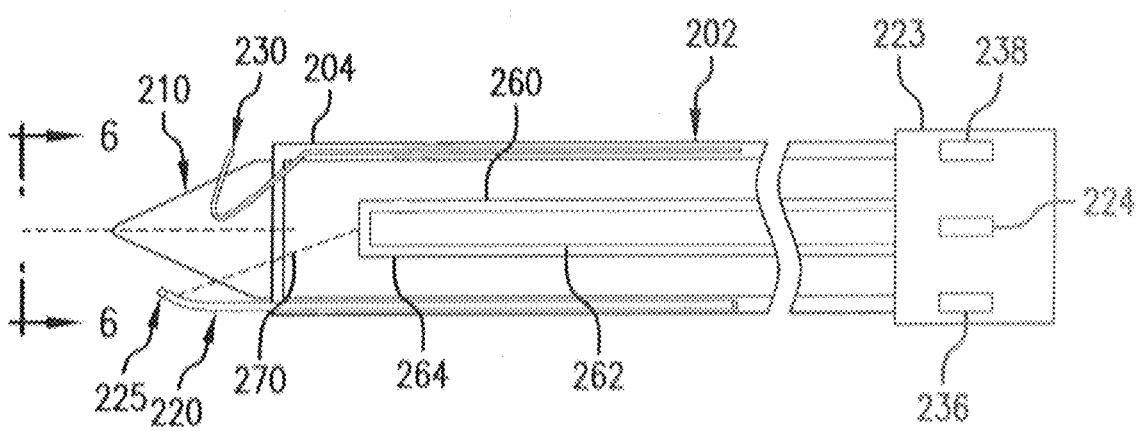
FIG. 2B illustrates the apparatus of FIG. 2A, particularly showing the retractor and the energy tool in partially-extended configurations.

FIGS. 2A and 2B illustrate another apparatus 200 for harvesting a vessel from a body (e.g., a human patient). The apparatus 200 includes a cannula 202 having a distal end 204 and a dissector 210 coupled to the distal end 204 of the cannula 202. The dissector 210 is configured for advancing along a target vessel to create a tunnel next to the vessel (e.g., from a skin incision of the patient, adjacent to the vessel to be harvested). The dissector 210 has a transparent portion for allowing an imaging device 260 housed in the cannula 202 to view therethrough. In one implementation, the dissector 210 has a cone shape, and an entirety of the cone shape dissector 210 may be transparent.

As shown in the figure, the apparatus 200 also includes an energy tool 220 moveably coupled to the cannula 202. The energy tool 220 is configured to separate a pediculated vessel having at least a segment of the vessel and a pedicle around the segment of the vessel. In some embodiments, the energy tool 220 may be configured to provide monopolar or bipolar radiofrequency (RF) energy for tissue separation and/or sealing. In other embodiments, the energy tool 220 may be configured to provide heat (e.g., inductive heating, resistive heating, Joule heating, etc.) for tissue separation and/or sealing. In further embodiments, the energy tool 220 may be configured to provide ultrasonic energy for tissue separation and/or sealing.

In the illustrated embodiments, the apparatus 200 has a proximal handle 223 with a control 224 for allowing a user to control a delivery of power to an energy delivery element 225 on the energy tool 220. For example, the control 224 may include one or more buttons for allowing the user to turn on the energy delivery element 225 to deliver energy, and to turn off the energy delivery element 225 to stop the delivery of energy. The control 224 may also include a button for allowing a user to adjust an amount of energy being delivered by the energy delivery element 225. During use, the handle 223 is coupled to a power source (not shown), which supplies power for the apparatus 200. In one implementation, the energy delivery element 225 may be one or more electrodes that provide RF energy. In another implementation, the energy delivery element 225 may be one or more heater elements that provide heat. In such cases, power may be supplied using a DC source to the heater element(s), which functions as resistive element(s) that heats up in response to the delivered direct current. In another implementation, the energy delivery element 225 may be one or more ultrasound applicators. In other embodiments, instead of implementing the control 224 at the handle 223, the control 224 may be implemented as a foot switch.

The energy tool 220 is configured to move between a retracted position (FIG. 2A) and an extended position (FIG. 2B). In the retracted position, at least a distal portion of the energy tool 220 is housed within the cannula 202. In the extended position, the distal portion of the energy tool 220 is outside the cannula 202. The apparatus 200 may include a control 236 at the handle 223 configured to move the energy tool 220 from the retracted position to the extended position and vice versa. For example, the control 236 may be a button that can be pushed distally to extend the energy tool 220 from the cannula 202, and be pulled proximally to retract the energy tool 220 back into the cannula 202.

Also, in some embodiments, the energy tool 220 is configured to rotate with respect to the cannula 202, so that the orientation of the energy tool 220 may be adjusted with respect to the cannula distal end 204. The control for energy tool rotation may be incorporated into control 236, or the apparatus 200 may include a separate control (not shown) at the handle 223 configured for rotating the energy tool 220. In other embodiments, the energy tool 220 may be configured to deflect towards a longitudinal axis 240 (see broken line in a plurality of the figures) of the apparatus 200/cannula 202 as the energy tool 220 moves from the retracted position to the extended position after deployed out of the cannula 202. For example, the energy tool 220 may include an elastic elongated body that has a bent configuration. In such cases, the energy tool 220 is configured to bend radially inward towards the longitudinal axis 240 of the apparatus 200 as the energy tool 220 is deployed distally, and is configured to return to a relatively more rectilinear configuration after it is retracted back within the cannula 202. This configuration is advantageous because it improves visibility of the energy tool 220 via the imaging device 260 housed inside the cannula 202. The imaging device 260 will be described in further detail below. In other embodiments, the distal end of the energy tool (which comprises the energy delivery element 225) may be curved or angled inward toward the longitudinal axis 240, for improved visibility by the imaging device 260. In other embodiments, the distal tip(s) of the energy tool 220 may be tapered, to facilitate use for blunt dissection of tissues. In other embodiments, the energy tool 220 may be slidably coupled to the cannula, so that the energy tool 220 can move along a path that is parallel to the longitudinal axis 240 after the energy tool 220 is deployed out of the cannula 202.

Figure 5:
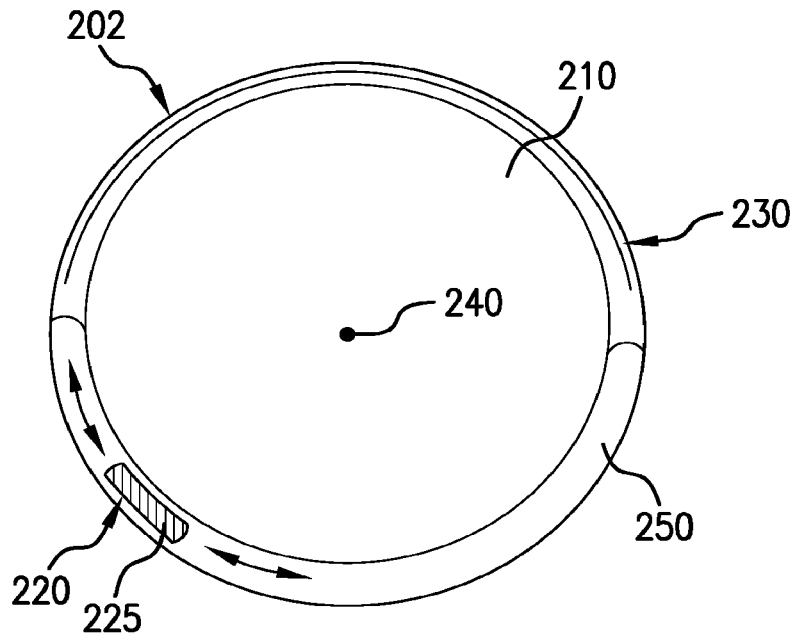
FIG. 5 illustrates a frontal view of the apparatus of FIG. 2A.
Figure 6:
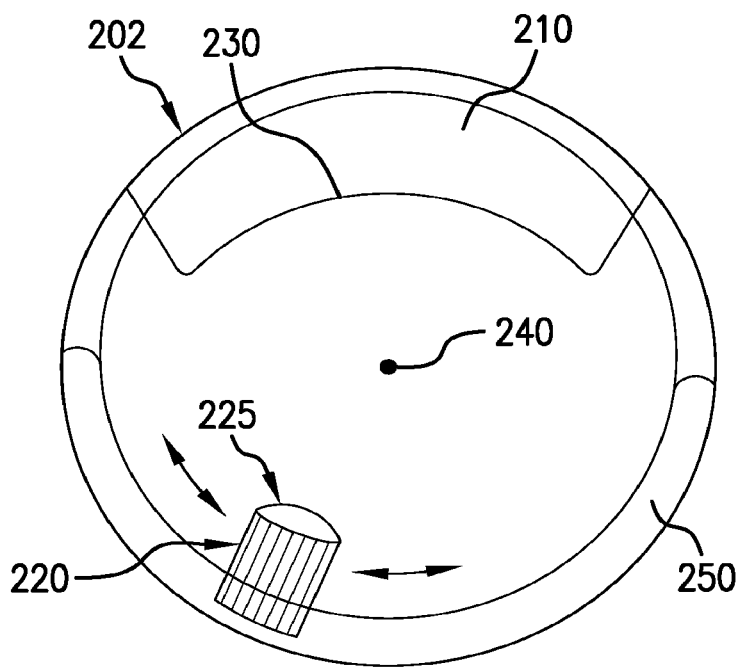
FIG. 6 illustrates a frontal view of the apparatus of FIG. 2B.

In the illustrated embodiments, the energy tool 220 is also moveable along a curvilinear path circumferentially around the longitudinal axis 240. In particular, as shown in FIG. 5, the energy tool 220 is housed in a curvilinear slot 250. The energy tool 220 may be extended out of the curvilinear slot 250 (FIG. 6), and may be moveable circumferentially around axis 240. This feature allows a user to place the energy tool 220 at a desired circumferential position with respect to the target tissue being operated on. This configuration also allows the energy tool 220 to move circumferentially around tissue surrounding a target vessel, and to separate such tissue from its surrounding tissue structure. The handle 223 of the apparatus 200 may have a control for allowing a user of the apparatus 200 to move the energy tool 220 circumferentially about the longitudinal axis 240 (or another axis) around the tissue. For example, the control may be a rotatable knob at the handle, which controls an amount of the circumferential movement of the energy tool 220. In one implementation, the control may be the control 236, and may include a button or a knob that can be slid (e.g., slid circumferentially) around a longitudinal axis of the handle 223 to thereby move the energy tool 220 within slot 250. In addition to being movable circumferentially, the energy tool 220 may also be rotatable so that its orientation with respect to the longitudinal axis 240 (or another axis) may be optimized for tissue harvest. The axis about which the energy tool 220 rotates may be a longitudinal axis of the energy tool 220 (e.g., an axis that extends through the energy tool 220), or may be an axis that is parallel and spaced away from the longitudinal axis of the energy tool 220. The control for rotation may be incorporated with the control 236, or may be a separate control on the handle (not shown).

In some embodiments, the control 236 for moving (and, in some embodiments, rotating) the energy tool 220 and the control 224 for activating the energy tool 220 may be integrated on a handle portion of the handle 223 that is configured to move relative to another part of the handle 223. In such cases, movement of the control 236 also results in movement of the control 224. In other embodiments, the control 236 and the control 224 may be separately implemented on the handle 223 such that movement of the control 236 will not cause a corresponding movement of the control 224.

As discussed, in some embodiments, the energy tool 220 may be configured to deflect towards the longitudinal axis 240 when it is deployed out of the cannula 102. Such feature, when combined with the circumferential movement of the energy tool 220 (and, in some embodiments, rotation of the energy tool 220) is particularly advantageous. This is because while movement of the energy tool 220 allows a pediculated vessel (having tissue surrounding the target vessel) to be isolated, the deflection of the energy tool 220 may allow a user to control a thickness of the tissue in the pediculated vessel that is surrounding the target vessel. For example, in some cases, the amount of deflection may be controlled based on a degree in which the energy tool 220 is extended out of the cannula 202. As the energy tool 220 is extended further out of the cannula 202, the end of the energy tool 220 may move closer to the longitudinal axis 240, and vice versa.

In some embodiments, the energy tool 220 is integrated with the cannula 202, and is provided as a component of the apparatus 200. In other embodiments, the apparatus 200 may not include the energy tool 220. In such cases, the cannula 202 may have a lumen sized for accommodating an energy tool, which may be a commercially available energy instrument that can be detachably coupled to the cannula 202. For example, a user of the apparatus 200 may select bipolar RF Maryland grasper forceps, VasoView HemoPro™ etc., as the energy tool 220, and may insert such energy tool 220 into the cannula 202 for the vessel harvesting procedure.

The energy tool 220 may have an arcuate tip, a blunt tip, a sharp tip, a spatulate tip, a tapered tip, a forceps-style tip (e.g., straight, curved, or angled jaws), or a tip having any of other configurations. Any of these tip configurations may be tapered toward their distal ends, to facilitate blunt dissection of tissues. Alternatively, or additionally, the energy tool 220 may have an edge configured to cut tissue. For example, the energy tool 220 may include a blade.

In some embodiments, the energy tool 220 may be steerable. For example, the distal end of the energy tool 220 may include one or more steering wires configured to apply tension to pull the distal end of the energy tool 220 to thereby steer the energy tool 220 in one or more directions. In such cases, the handle of the apparatus 200 may include a steer control for allowing the user of the apparatus 200 to bend the distal end of the energy tool 220 in a desired direction.

Figure 2C:
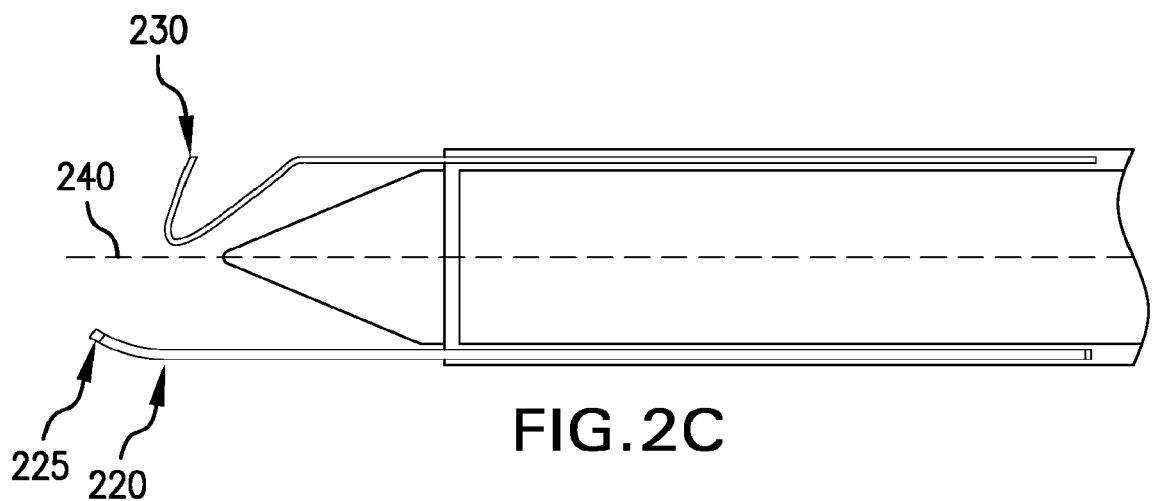
FIG. 2C illustrates the apparatus of FIG. 2A and FIG. 2B, particularly showing the retractor and the energy tool in fully-extended configurations.

As shown in FIG. 2A, 2B, and 2C, the apparatus 200 further includes a retractor 230 moveably coupled to the cannula 202. The retractor 230 is configured to engage with a portion of the pediculated vessel, and may be used to manipulate the portion of the pediculated vessel while the energy tool 220 is being used to operate on tissue to create other portion of the pediculated vessel. In some embodiments, the retractor 230 may be configured to lift the target vessel from the underside of the apparatus 200 to a position that improves visualization via the imaging device 260 of the target vessel and of the area to be treated (tissues to be harvested). This allows target tissue (that is to be operated by the energy tool 220) to be visible within the field of view of the imaging device 260, rather than being obscured from view by the previously-harvested segment of target vessel.

The retractor 230 is configured to move from a retracted position (FIG. 2A), to a partially-extended position (FIG. 2B), and to a fully-extended position (FIG. 2C), or vice versa. In the retracted position, at least a distal portion of the retractor 230 is housed within the cannula 202. In the extended positions, the distal portion of the retractor 230 is outside the cannula 202. The apparatus 200 may include a control 238 at the handle 223 configured to move the retractor 230 from the retracted position to the extended position and vice versa. For example, the control 238 may be a button that can be pushed distally to extend the retractor 230 from the cannula 202, and be pulled proximally to retract the retractor 230 back into the cannula 202.

As shown in the figure, the cannula 202 has a first side 232 and a second side 234 opposite from the first side 232, and wherein retractor 230 is located closer to the first side 232 of the cannula 202 than to the second side 234 of the cannula 202, and the energy tool 220 is located closer to the second side 234 of the cannula 202 than to the first side 232 of the cannula 202.

Figure 2D:
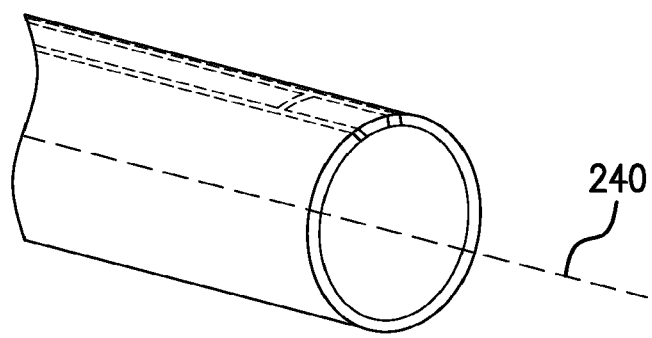
FIG. 2D illustrates the retractor having a lower-profile when in a retracted position.
Figure 2E:
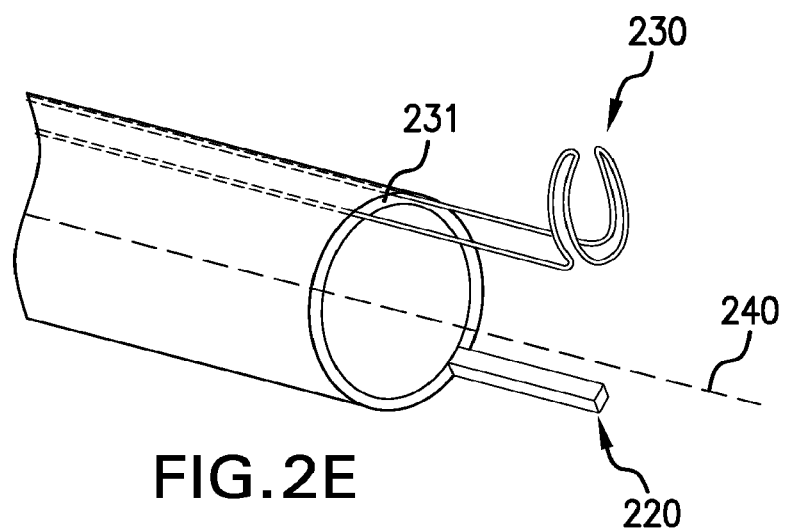
FIG. 2E illustrates the retractor having a larger-profile when in an extended position.

In the illustrated embodiments, the retractor 230 is configured to translate along a path that is parallel to a longitudinal axis 240 of the apparatus 200/cannula 202 as the retractor 230 moves from its retracted position to its extended position. In other embodiments, the retractor 230 is configured to deflect away from the longitudinal axis 240 as the retractor 230 moves from its retracted position to its extended position. In other embodiments, the retractor 230 may be configured to change from a lower-profile (e.g., with a collapsed geometry) when in a retracted position (FIG. 2D) in a slot 231 to receive the retractor, to a larger-profile (e.g., with an expanded geometry) when in an extended position in which the retractor 230 is extended from the cannula 202 (FIG. 2E). In some cases, the retractor 230 may comprise an elastic material, such as nitinol or a shape-memory alloy. In one implementation, the retractor 230 may include a spring wire.

In other embodiments, the retractor 230 is optional, and the apparatus 200 may not include the retractor 230.

Figure 3:
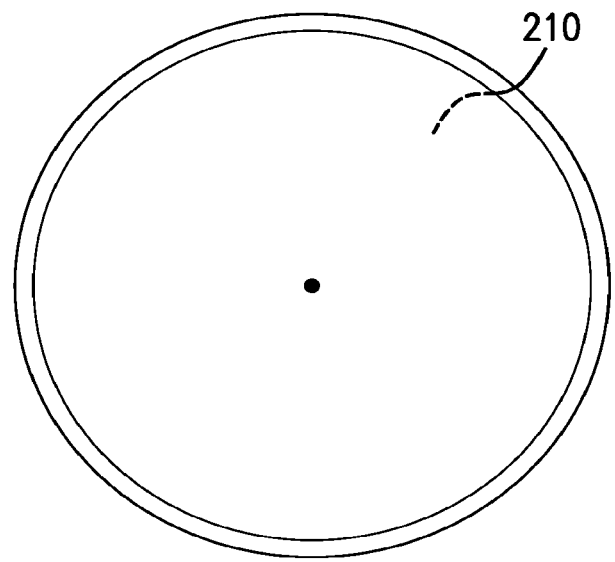
FIG. 3 illustrates an image from an imaging device viewing through a dissector of the apparatus of FIG. 2A when the retractor and the energy tool are in retracted configurations.
Figure 4:
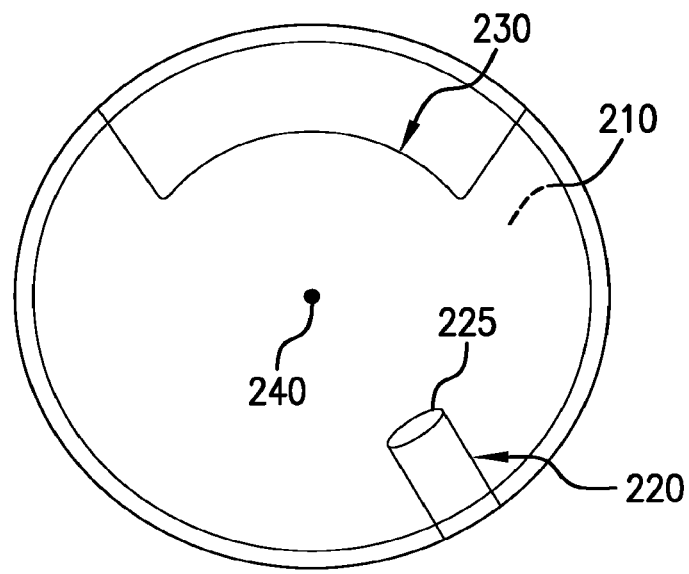
FIG. 4 illustrates an image from an imaging device viewing through a dissector of the apparatus of FIG. 2B when the retractor and the energy tool are in extended configurations.

As shown in FIG. 2A, both the retractor 230 and the energy tool 220 are in retracted configurations. In this arrangement, the cannula 200 may be more easily inserted through a skin incision into the patient. FIG. 3 illustrates an image from the imaging device 260 viewing through the dissector 210 of the apparatus 200 when the retractor 230 and the energy tool 220 are in retracted configurations. After the distal end 204 of the cannula 200 has been inserted into the patient and a short length of tunnel dissected adjacent to the target vessel, the retractor 230 and/or the energy tool 220 may be deployed into extended configurations (FIG. 2C). FIG. 4 illustrates an image from an imaging device viewing through a dissector of the apparatus of FIG. 2B when the retractor and the energy tool are in extended configurations. In the configuration shown in FIG. 2B, at least a part of the retractor 230 and/or at least a part of the energy tool 220 is visible through the transparent portion of the dissector 210.

As shown in FIG. 2A, the apparatus 200 further includes a lumen 262 in the cannula 202 configured for housing the imaging device 260. The lumen 262 has a distal end 264, and the energy delivery element 225 of the energy tool 220 can be extended distal of the lumen distal end 264 and distal end 268 of the imaging device 260. Having the energy tool 220 be distal to the imaging device 260 during use of the energy tool 220 is advantageous because it allows the energy tool 220 to be viewable by the imaging device 260 while the energy tool 220 is operating on tissue. As shown in FIG. 2B, the imaging device 260 has a distal end 268, and the energy tool 220 (i.e., the operative part of the energy tool 220) has been extended distal to the distal end 268 of the imaging device 260. Also, as shown in FIG. 2B, an axis 270 extending from the distal end 268 of the imaging device 260 to the energy tool 220 traverses the transparent portion of the dissector 210. This allows the energy tool 220 to be viewable by the imaging device 260 through the transparent portion of the dissector 210. The imaging device 260 may be an endoscope (with lens and/or fiber optics), or may be an electronic image sensor (such as a CMOS device).

Figure 14:
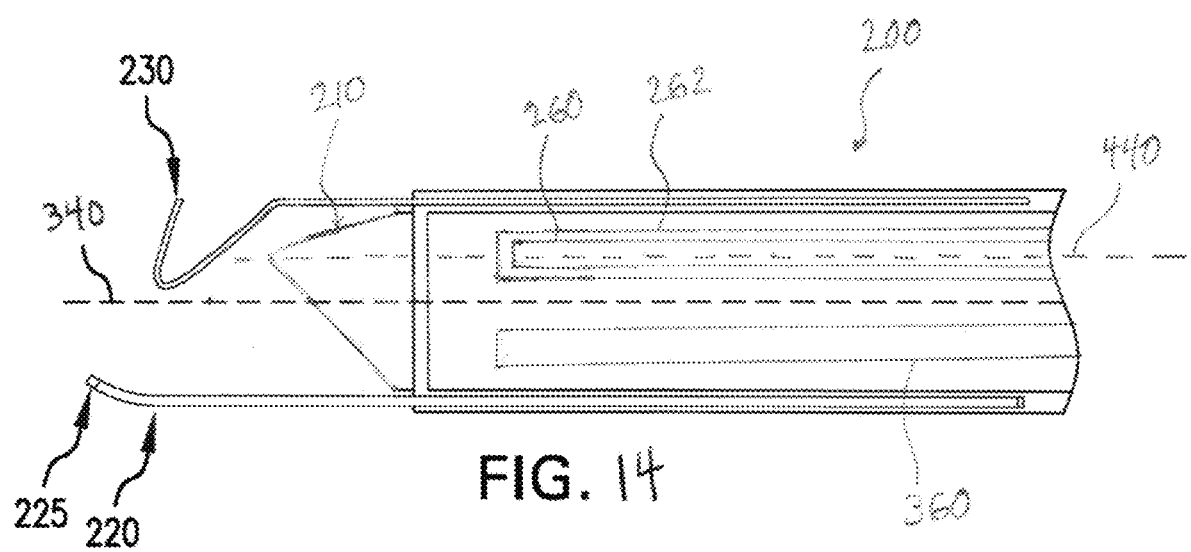
FIG. 14 illustrates another apparatus for harvesting a vessel, particularly showing the retractor and the energy tool in fully-extended configurations.

In some embodiments, such as the embodiment shown in FIG. 14, the apparatus 200 may further optionally include a second imaging device 360. In such cases, the first imaging device (imaging device 260) may be configured for visualization of tissue dissection by the dissector 210, and the second imaging device 360 may be configured for visualization of an operation being performed by the energy tool 220. The first and second imaging devices may be two endoscopes (e.g., with rod lens or fiber optics). Alternatively, one or each of the first and second imaging devices may include an electronic image sensor (e.g., CMOS device).

In the above embodiments, the longitudinal axis 240 of the apparatus 200/cannula 202 is illustrated as corresponding with the dissector 210. In other embodiments, the apparatus 200/cannula 202 may have a longitudinal axis that is offset from the dissector 210. For example, in some embodiments, such as the embodiment shown in FIG. 14, the apparatus 200/cannula 202 may have a central axis 340 extending along a longitudinal length of the apparatus 200, the dissector 210 is located at a first longitudinal axis 440 offset from the central axis 340, and the energy tool 220 is located at a second longitudinal axis offset from the central axis, the second longitudinal axis being different from the first longitudinal axis. In such cases, the apparatus 200 may have two imaging devices associated with the dissector 210 and the energy tool 220, respectively. For example, in the embodiment shown in FIG. 14, the apparatus 200 may have a first imaging device 260 located at or close to the first longitudinal axis 440 so that the first imaging device may be used to view the dissector 210 as the dissector 210 is operating on tissue. Similarly, the second imaging device 360 may be located at or close to the second longitudinal axis so that the second imaging device 360 may be used to view the energy tool 220 as the energy tool 220 is operating on tissue. The above feature is advantageous because during pedicle isolation, the energy tool 220 and the tissue being operated on may be visualized without the dissection tip 210 material in between them, which provides a clearer image of the endoscopic space during operation by the energy tool 220.

A method for harvesting a vessel will now be described with reference to the apparatus 200. The method will be described with reference to FIGS. 7-12 which illustrate images provided from the imaging device 260 viewing through the dissector 210 of the apparatus of FIG. 2A during a vessel harvesting procedure.

First, a skin of a patient is incised to create an entry point and to expose target vessel at the entry point (a proximal end of an endoscopic tunnel).

Next, a short length of the vessel at the entry point is mobilized. For example, such may be accomplished by dissecting around the entire circumference of the vessel at the entry point using standard surgical techniques.

Next, the apparatus 200 is inserted at the entry point.

Figure 7:
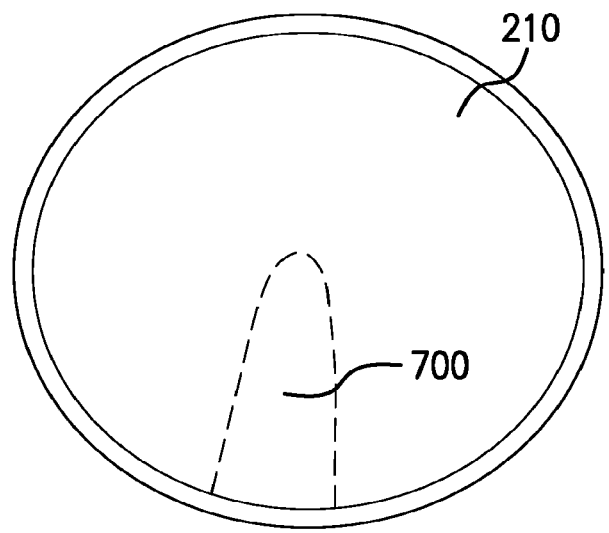
FIGS. 7-9 illustrate images from an imaging device viewing through a dissector of the apparatus of FIG. 2 during a vessel harvesting procedure.
Figure 8:
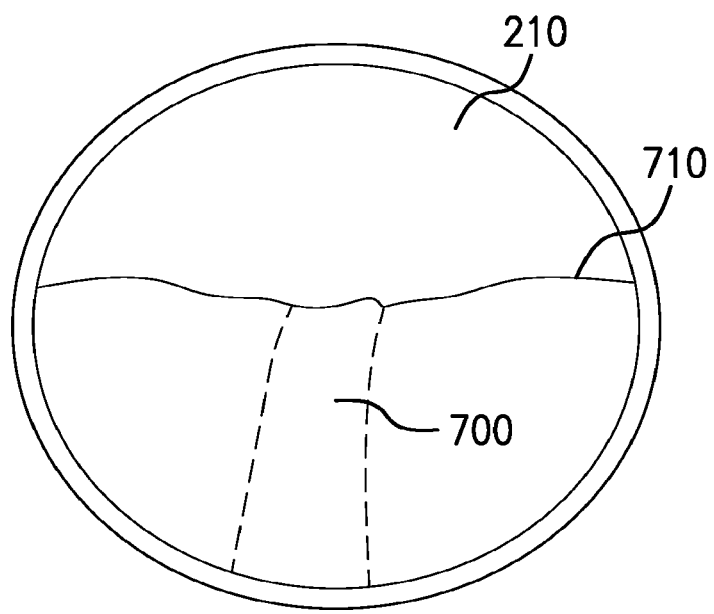

Next, the apparatus 200 is advanced, while the dissector 210 is used to dissect a short length of tissue 700 along upper side of target vessel. An image obtained by the imaging device 260 viewing through the dissector 210 is shown in FIG. 7, particularly showing the short length of tissue 700 along the upper side of a target vessel. While the apparatus 200 is advanced, the energy tool 220 and the retractor 230 are retracted within the cannula 202. As shown in FIG. 8, as the dissector 210 is advanced distally further, the image will show an extent 710 of the dissection.

Figure 9:
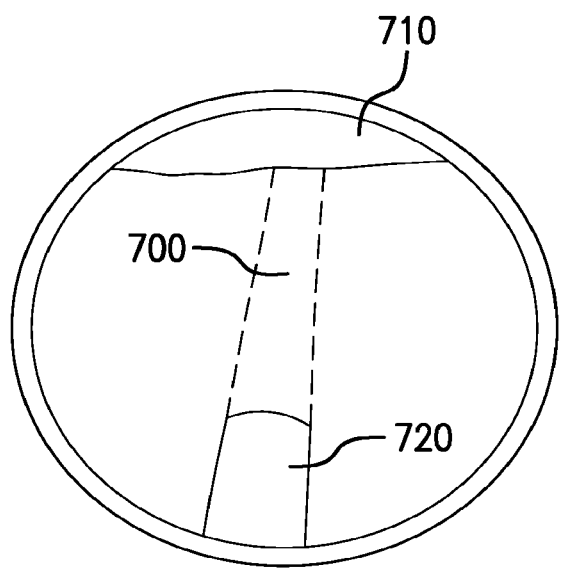

Next, the apparatus 200 is retracted proximally so that the exposed length of tissue 700 and the mobilized section of the vessel at the entry point are in view through the transparent portion of the dissector 210. An image obtained by the imaging device 260 viewing through the dissector 210 is shown in FIG. 9, particularly showing the extent 710 of the dissection, the tissue 700 along the upper side of the vessel, and the mobilized length 720 of the vessel.

Figure 10A:
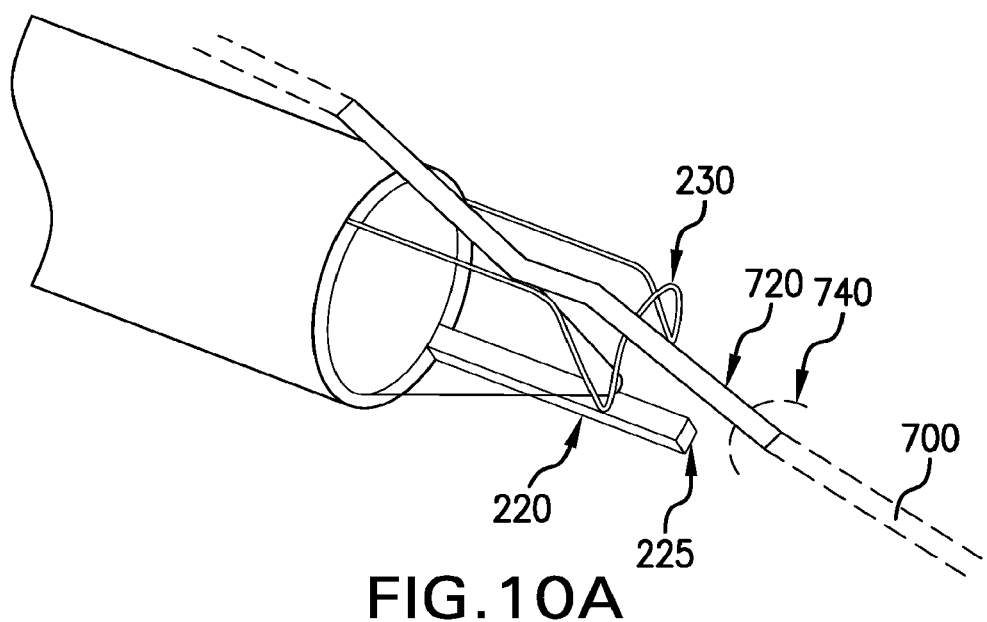
FIGS. 10A-10B illustrate engagement of the vessel by a retractor during the vessel harvesting procedure.
Figure 10B:
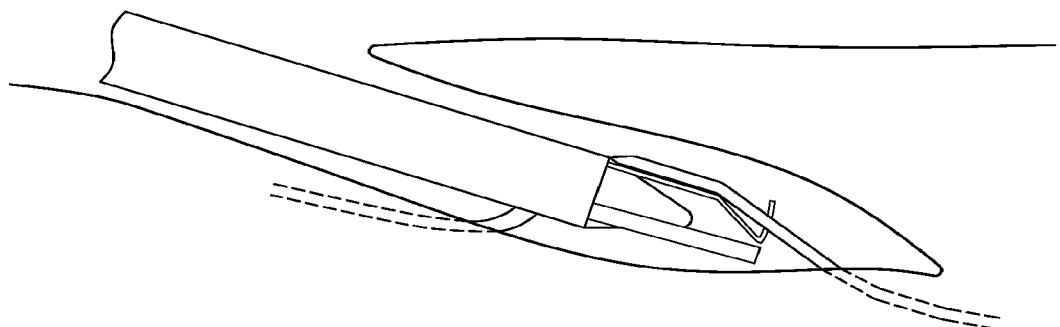
Figure 10C:
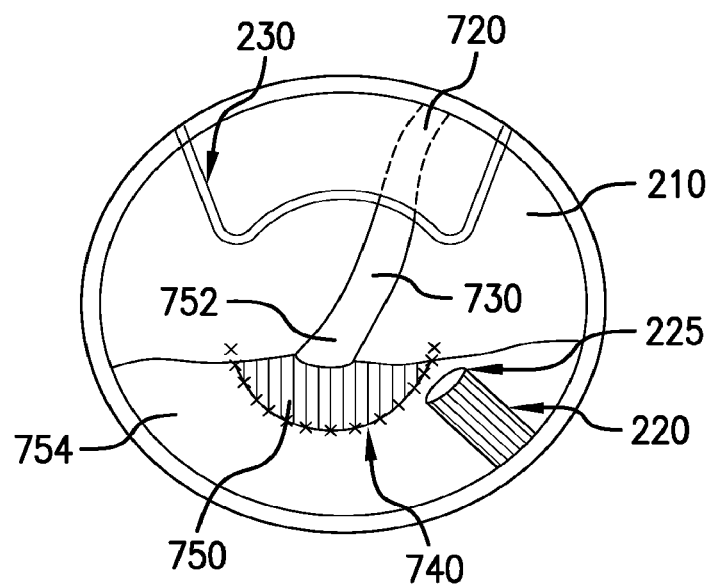

Next, the retractor 230 is extended, and is positioned to engage against the mobilized length 720 of vessel at the entry point. The retractor 230 may be used to apply upward traction on the vessel. Thus, the positioning of the vessel may be affected by manipulation of the retractor 230. In some cases, the degree of extension of the retractor 230 may be adjusted to vary the position of the vessel. The energy tool 220 is also extended from the cannula 202, and is positioned along the vessel underside, while the retractor 230 is "lifting" the vessel, as shown in FIG. 10A and FIG. 10B. An image obtained by the imaging device 260 viewing through the dissector 210 is shown in FIG. 10C, particularly showing both the retractor 230 and the energy tool 220 extended from the cannula 202. As shown in the figure, in the extended configuration, the energy tool 220 is visible by the imaging device 260 viewing through the transparent portion of the dissector 210. This allows the user of the apparatus 200 to view the tissue on which the energy tool 220 is operating. While the retractor 230 is lifting the mobilized length 720 of the vessel, the underside 730 of the mobilized length 720 of the vessel can be seen through the dissector 210 by the imaging device 260. The user may then operate the energy device 220 to make a circumferential tissue separation 740 (and also sealing of blood vessels encountered during tissue separation) to separate tissue 750 (containing the target vessel 752) from its surrounding tissue 754. In particular, the energy tool 220 may be moved substantially circumferentially (e.g., through a circumferential range that is more than 150°, or more than 180°, or more than 270°, more than 300°, etc., or 360°) around the tissue 750 that is surrounding the target vessel 752 to thereby circumferentially separate a pediculated segment of vessel. In some cases, the energy tool 220 may also be rotated to optimize the orientation of the energy delivery element 225 for tissue harvest.

Figure 11:
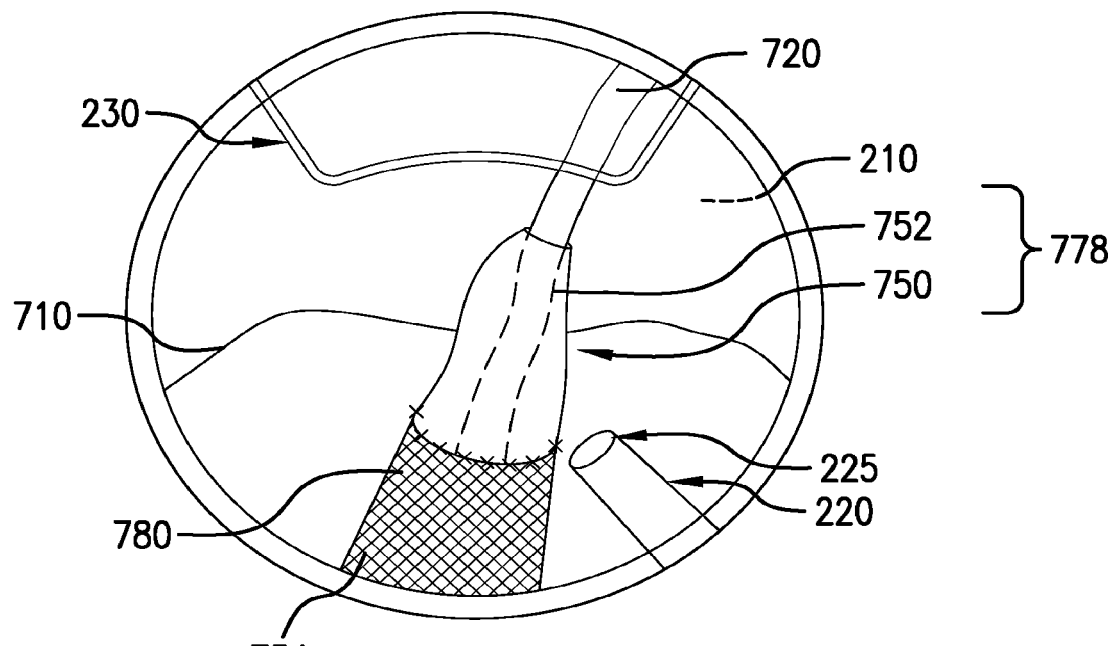

The energy tool 220 may be used to bluntly dissect tissue below the vessel 752. In some cases, if the energy tool 220 has a blade, the blade may be used to sharply dissect tissue below the vessel 752. Alternatively, or additionally, the energy tool 220 may be activated to separate the tissue surrounding the vessel 752. Also, the energy tool 220 may be activated to seal and sever branches of the target vessel, and/or to control localized bleeding during the tissue harvest. In some cases, the energy tool 220 may also be advanced and/or retracted and/or rotated or otherwise manipulated to optimize placement of the energy tool 220 at desired position(s) and/or orientations with respect to the target tissue. The energy tool 220 may be selectively manipulated and/or selectively activated to deliver energy until a desired length of pediculated vessel has been completely separated from the surrounding tissues. For example, as the energy tool 220 is being used to separate tissue 750 surrounding the target vessel 752 from the surrounding tissue 754, the cannula 202 and/or the energy tool 220 may be advanced to separate a length (along the longitudinal axis of the vessel) of tissue 750 from the surrounding tissue 754. An image obtained by the imaging device 260 viewing through the dissector 210 is shown in FIG. 11, particularly showing a length of pediculated vessel 778, which includes tissue 750 surrounding the target vessel 752. The mobilized length 720 of the vessel at the tunnel entry is also shown. Also, the surrounding tissue 754 (in a form of a channel 780) from which the tissue 752 is dissected is visible in the image. The channel 780 is a result of the length of the pediculated vessel 778 having separated from its surrounding tissue 754.

After the segment of the pediculated vessel has been completely separated from the surrounding tissues 754, the energy tool 220 and the retractor 230 are retracted into the cannula 202 to avoid inadvertent injury to the harvested tissue.

Figure 12:
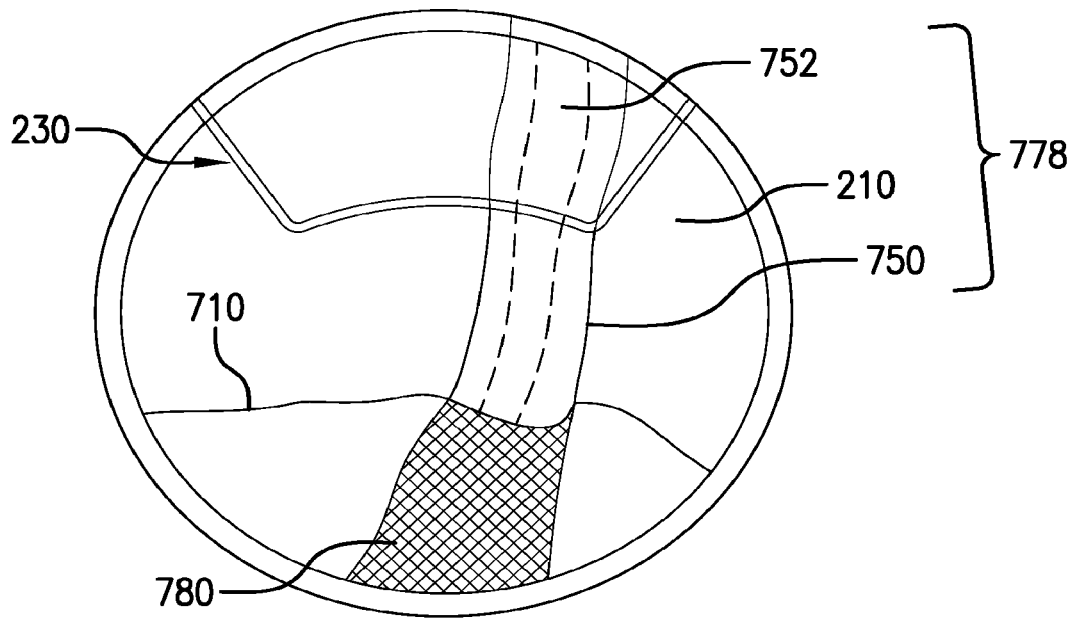

The above acts (i.e., advancing the cannula 202 to expose tissue above a length of target vessel, retracting the cannula 202, extending the retractor 230, extending the energy tool 220, using the energy tool 220 to separate tissue, retracting the retractor 230 and the energy tool 220) are repeated until a desired length of pediculated vessel 778 has been isolated. An image obtained by the imaging device 260 viewing through the dissector 210 is shown in FIG. 12, particularly showing a desired length of pediculated vessel 778 that has been harvested. The pediculated vessel 778 includes tissue 750 surrounding the target vessel 752.

Next, opposite ends of the isolated pediculated vessel are severed, and the harvested pediculated vessel is removed from the endoscopic tunnel.

The apparatus 200 and the above harvesting technique are advantageous in several aspects. First, when the retractor 230 and the energy tool 220 are extended distally relative to the cannula 202, they are visible by the imaging device 260 viewing through the dissector 210. Accordingly, the area undergoing treatment, i.e., tissue being sealed and cut by the energy tool, is fully visible by the user of the apparatus 200 during this portion of the procedure. This overcoming one of the main safety concerns exists in the apparatus 10 of FIG. 1.

Also, because the energy tool 220 is selectively activated by the user via the control 224 at the handle 223, or by other methods (e.g., foot switch), the user is able to control when thermal energy is (or is not) applied to the tissue. Accordingly, the user is able to both precisely locate tissue to be operated on (i.e., via the imaging device 260 that views the tissue), and time energy delivery to the target tissue (i.e., via the control 224), rather than delivering energy continuously and indiscriminately to all tissue in contact with the cutting element of the apparatus 10 of FIG. 1. The ability to allow control of timing of energy delivery is advantageous. With the exception of procedures intended to induce cell necrosis (e.g., tissue ablation), it is desirable for safety and effectiveness to limit hyperthermic exposure of both the target and adjacent tissues. In the case of EVH, the ability to control the timing of energy delivery minimizes the risk of thermal injury to the CABG graft, injury that could negatively affect graft patency and revascularization efficacy.

In addition, with visibility of the area undergoing treatment, and with control of the timing and location of energy delivery provided by the energy tool 220, the user is thus able to tailor his or her actions to optimize tissue sealing and cutting. For example, based on what the user can see through the transparent dissector 210, the user may decide to bluntly and/or sharply dissect tissue with the energy tool without applying energy with the energy tool 220, if needed. This minimizes the risk of inadvertent thermal injury to the harvested vessel.

Furthermore, the apparatus 200 and the method 1300 are advantageous because they allow a user to obtain a pediculated vessel 778 that includes the harvested vessel 752 surrounded by a layer of tissue 750. Harvested vessel 752 that includes a surrounding perivascular tissue (tissue pedicle) may lead to improved long-term bypass graft patency, and therefore is advantageous over skeletonized vessel that does not have any tissue pedicle. The pediculated or "no-touch" harvesting technique and the resulting pediculated vessel may improve long-term performance of venous conduits used in CABG by protecting the vessel from mechanical trauma during harvest, providing structural support to the conduit and allowing perfusion of the conduit wall upon arterialization, and facilitating beneficial biochemical processes such as nitric oxide release.

FIG. 13 illustrates a method 1300 for harvesting a vessel from a body. First, an endoscopic space adjacent to a vessel to be harvested is created by a dissector, the dissector having a transparent portion (item 1304). In some embodiments, the dissector may be the dissector 210 described herein. Next, a pediculated vessel (having at least a segment of the vessel and a pedicle around the segment of the vessel) is separated by an energy tool, wherein at least a part of the energy tool is visible through the transparent portion of the dissector while the energy tool is being used (item 1306). In some embodiments, the energy tool may be the energy tool 220 described herein.

It should be noted that the energy tool 220 should not be limited by the examples of configurations discussed previously, and that the energy tool 220 may have other configurations in other embodiments. The energy tool 220 in FIG. 7 through FIG. 12 is shown as a monopolar RF electrode tip for simplicity (similar to one used for open-access, pediculated harvest of an internal thoracic artery), but can also be a forceps-type instrument such as VasoView HemoPro, or any other type of instrument configuration suitable for tissue coagulation and separation. For example, in other embodiments, the energy tool 220 may include a ring shape structure (e.g., the cutting element 16 described with reference to the apparatus 10 of FIG. 1). The ring-shape structure may be mounted to a rod. Also, in some cases, the energy tool 220 may also include a first heating element at a leading end of the ring-shape structure, and a second heating element at a circumferential exterior surface of the ring-shape structure for providing energy to control bleeding. The second heating element may be proximal to the first heating element. The first and second heating elements may be selectively activated to perform different functions. For example, the first heating element may be selectively activated (e.g., by actuation of a first control at the handle 223) to cut tissue that is in contact by the leading end of the ring-shape structure as the ring-shape structure is advanced distally, and the second heating element may be selectively activated (e.g., by actuation of a second control at the handle 223) to control bleeding from tissue that has been cut by the leading end of the ring-shape structure.

In the embodiments disclosed a trocar such as a blunt tip trocar as described in U.S. Pat. No. 6,811,546, patent application Ser. No. 09/648660 filed Aug. 25, 2000 (herein incorporated by reference in its entirety), may be utilized and inserted through the incision or insertion point prior to the apparatus being introduced into the patient.

Although particular embodiments have been shown and described, it will be understood that they are not intended to limit the claimed inventions, and it will be understood to those skilled in the art that various changes and modifications may be made without departing from the spirit and scope of the claimed inventions. The claimed inventions are intended to cover alternatives, modifications, and equivalents.

What is claimed is:

1. A method for harvesting a vessel from a body, comprising: creating, by an apparatus, a tunnel from a skin incision for harvesting the vessel, wherein the apparatus comprises:
   a first imaging device;
   a cannula having a distal end, and a dissector for advancing along the vessel to create the tunnel, wherein the dissector is coupled to the distal end of the cannula and the dissector includes a transparent portion, wherein the cannula comprises a lumen housing the first imaging device;
   an energy tool moveably coupled to the cannula; and
   a second imaging device having a distal end;
   wherein the first imaging device is disposed to visualize tissue dissection by the dissector, wherein the visualization of the tissue dissection can only occur through the transparent portion of the dissector, and wherein the second imaging device is disposed to visualize an operation performed by the energy tool, wherein the visualization of the operation can only occur through the transparent portion of the dissector; and
   wherein an axis extending from the distal end of the second imaging device to the energy tool traverses the transparent portion of the dissector during use of the energy tool, and wherein the apparatus has a central axis extending along a longitudinal length of the apparatus, the dissector is located at a first longitudinal axis offset from the central axis, and the energy tool is located at a second longitudinal axis offset from the central axis, wherein the second longitudinal axis is different from the first longitudinal axis; and
   separating from surrounding tissue, by the energy tool, a pediculated vessel having at least a segment of the vessel and a pedicle around the segment of the vessel, wherein at least a part of the energy tool is visible through the transparent portion of the dissector while the energy tool is being used.

2. The method of claim 1, wherein the energy tool has a retracted position and an extended position.

3. The method of claim 1, wherein the energy tool is steerable.

4. The method of claim 1, wherein the energy tool has an arcuate tip, a blunt tip, or a spatulate tip.

5. The method of claim 1, wherein the energy tool is rotatable to modify its orientation with respect to the central axis of the apparatus.

6. The method of claim 1, wherein the apparatus further comprises a retractor moveably coupled to the cannula, wherein the retractor is configured to engage with the pediculated vessel.

7. The method of claim 6, wherein the retractor is moveable to a position distal to a distal end of the first imaging device.

8. The method of claim 6, wherein the cannula has a first side and a second side opposite from the first side, and wherein the retractor is located closer to the first side of the cannula than to the second side of the cannula, and the energy tool is located closer to the second side of the cannula than to the first side of the cannula.

9. The method of claim 6, wherein the retractor is configured to deflect away from the central axis of the apparatus as the retractor moves from a retracted position to an extended position.

10. The method of claim 1, wherein the energy tool is configured to provide radiofrequency energy for tissue separation and/or sealing.

11. The method of claim 1, wherein the energy tool is located distal to a distal end of the lumen.

12. The method of claim 1, wherein the first imaging device comprises an endoscope.

13. The method of claim 1, wherein the first imaging device comprises an electronic image sensor.

* * * * *